United States Patent
Bergmann et al.

(10) Patent No.: US 9,261,517 B2
(45) Date of Patent: *Feb. 16, 2016

(54) DIAGNOSIS OF ACUTE CORONARY SYNDROME, MYOCARDIAL INFARCTION, OR ANGINA PECTORIS BY MEANS OF NEUROPHYSIN II

(71) Applicant: BRAHMS GmbH, Hennigsdorf (DE)

(72) Inventors: Andreas Bergmann, Berlin (DE); Nils Morgenthaler, Berlin (DE); Jana Papassotiriou, Berlin (DE); Joachim Struck, Berlin (DE); Leong L. Ng, Leicester (GB)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/951,084

(22) Filed: Jul. 25, 2013

(65) Prior Publication Data

US 2013/0344513 A1    Dec. 26, 2013

Related U.S. Application Data

(63) Continuation of application No. 12/447,105, filed as application No. PCT/DE2007/001928 on Oct. 26, 2007, now Pat. No. 8,501,485.

(30) Foreign Application Priority Data

Oct. 26, 2006 (DE) .......................... 10 2006 050 497
Dec. 4, 2006 (DE) .......................... 10 2006 057 409

(51) Int. Cl.
*G01N 33/68* (2006.01)
*G01N 33/74* (2006.01)

(52) U.S. Cl.
CPC ............ *G01N 33/74* (2013.01); *G01N 33/6893* (2013.01); *G01N 2410/04* (2013.01); *G01N 2800/324* (2013.01)

(58) Field of Classification Search
USPC ..................................... 436/86; 435/7.1, 7.94
See application file for complete search history.

(56) References Cited

U.S. PATENT DOCUMENTS

| 7,790,397 B2 * | 9/2010 | Hamm et al. ................... 435/7.1 |
| 8,501,485 B2 * | 8/2013 | Bergmann et al. .............. 436/86 |
| 2005/0136455 A1 | 6/2005 | Lehmann et al. |
| 2008/0057590 A1 * | 3/2008 | Urdea et al. ..................... 436/71 |
| 2009/0155827 A1 * | 6/2009 | Zeiher et al. .................... 435/15 |
| 2009/0221009 A1 | 9/2009 | Bergmann et al. |
| 2010/0041064 A1 | 2/2010 | Bergmann et al. |
| 2010/0093012 A1 | 4/2010 | Bergmann et al. |
| 2011/0039283 A1 | 2/2011 | Bermann et al. |
| 2011/0229911 A1 * | 9/2011 | Bergmann et al. ............. 435/7.4 |
| 2011/0263821 A1 | 10/2011 | Bergmann et al. |
| 2012/0270245 A1 * | 10/2012 | Bergmann et al. ........... 435/7.92 |

FOREIGN PATENT DOCUMENTS

| CA | 2428760 A1 | 11/2003 |
| EP | 1363128 A2 | 11/2003 |
| EP | 1628136 A1 | 2/2006 |
| EP | 1666881 A2 | 6/2006 |
| WO | WO-2004/006860 A2 | 1/2004 |
| WO | WO-2006/018315 A1 | 2/2006 |
| WO | WO 2008/049422 | * 5/2008 |

OTHER PUBLICATIONS

Khan, S. et al. C-Terminal Provasopressin (Copeptin) as a Novel and Prognostic Marker in Acute MI. Circulation 115(16)2103-2110, Apr. 24, 2007.*

Khan et al., "C-terminal proVasopressin (copeptin) as a novel and prognostic marker in acute myocardial infarction—The Leicester Acute Myocardial Infarction Peptide (LAMP) Study", Circulation American Heart Association, Abstract, 2006.

Khan et al., "C-terminal provasopressin (copeptin) as a novel and prognostic marker in acute myocardial infarction Leicester acute myocardial infarction peptide (LAMP) study", vol. 115, No. 16, pp. 2103-2110, 2007.

Chute, J.P., "A Metabolic Study of Patients with Lung Cancer and Hyponatremia of Malignancy," Clin Cancer Res vol. 12, No. 3, pp. 888-896, Feb. 1, 2006.

Nakamura, T., "Possible vascular role of increased plasma arginine vasopressin in congestive heart failure," International Journal of Cardiology, vol. 106, pp. 191-195, 2006.

North, W. et al., "Isolation and Partial Characterization of Two Human Neurophysins . . . " *J. Clinical Endocrinology Metabolism* 51(4), 884-891.

Pullan, P. et al., "Plasma Vasopressin and Human Neurophysins in Physiological . . . " *J Clinical Endocrinology Metabolism* 49(4), 580-587.

* cited by examiner

*Primary Examiner* — Ralph Gitomer
(74) *Attorney, Agent, or Firm* — Novak Druce Connolly Bove + Quigg LLP

(57) ABSTRACT

The invention relates to methods for in vitro diagnosis of acute coronary syndrome (ACS), acute myocardial infarction (AMI) or angina pectoris (AP) by determining the level of neurophysin II in a sample from a patient.

9 Claims, 3 Drawing Sheets

Figure 3.

Preprovasopressin amino acid sequence:

```
MPDTMLPACF LGLLAFSSAC YFQNCPRGGK PAMSDLELRQ CLPCGPGGKG RCFGPSICCA      60
DELGCFVGTA EALRCQEENY LPSPCQSGQK ACGSGGRCAA FGVCCNDESC VTEPECREGF     120
HRRARASDRS NATQLDGPAG ALLLRLVQLA GAPEPFEPAQ PDAY                      164
```

| | |
|---|---|
| 1-19 | Signal sequence |
| 20-28 | ARG-VASOPRESSIN |
| 32-124 | NEUROPHYSIN 2 |
| 126-164 | COPEPTIN |

DIAGNOSIS OF ACUTE CORONARY SYNDROME, MYOCARDIAL INFARCTION, OR ANGINA PECTORIS BY MEANS OF NEUROPHYSIN II

RELATED APPLICATIONS

This application is a continuation of U.S. application Ser. No. 12/447,105, filed Sept. 22, 2009, now U.S. Pat. No. 8,501,485, which is a national stage application (under 35 U.S.C. §371) of PCT/DE2007/001928, filed Oct. 26, 2007, which claims benefit of German application 102006050497.6, filed Oct. 26, 2006 and German application 102006057409.5, filed Dec. 4, 2006. The entire contents of each of these applications are hereby incorporated by reference herein.

BACKGROUND OF THE INVENTION

The invention relates to a method for risk stratification for acute coronary syndrome (ACS), in particular acute myocardial infarction (AMI) and angina pectoris (AP), wherein provasopressin (proAVP) or fragments and partial peptides thereof, in particular copeptin or neurophysin II, is determined by an in vitro diagnosis. The invention further relates to suitable combinations of biomarkers for in vitro diagnostics.

Risk stratification is becoming increasingly important for cardiac disease in symptomatic as well as asymptomatic patients. In particular for acute coronary syndrome there is a great need for suitable risk stratification.

Risk stratification is used to identify patients with an unfavorable prognosis, for intensive diagnostics, and for therapy/treatment, with the objective of enabling an optimal clinical outcome. Accordingly, the aim of suitable risk stratification is to follow effective treatment methods for acute coronary syndrome, using percutaneous coronary intervention and the newest medicaments.

Appropriate treatment requires early diagnosis and differentiation of acute coronary syndrome, even upon emergency room admission, in conjunction with clinical decisions. Due to nonspecific symptoms such as chest pain in acute coronary syndrome, the differentiation and delineation from other diseases as well as the identification of acute coronary syndrome are essential.

In the prior art, the use of biochemical markers, in particular classical markers such as cardiac troponin, myoglobin, and CK-MB mass, has been attempted for prognosis of myocardial infarction (Katus, H. A.; Remppis, A.; Scheffold, T.; Diederich, K. W., and Kuebler, W. (1991): Intracellular compartmentation of cardiac troponin T and its release kinetics in patients with reperfused and nonreperfused myocardial infarction, Am J Cardiol 67 (16): 1360-1367). Type B natriuretic peptide (BNP) together with pro-BNP (NT-ProBNP) (EP 1363128 B1, EP 1666881 A2) has proven to be another effective biochemical marker in myocardial diagnostics.

Copeptin (also referred to as C-terminal proAVP) has been described in WO 2006/018315 (BRAHMS AG) as a biomarker for in vitro diagnosis of AMI. A corresponding copeptin assay is disclosed in Morgenthaler et al. (Nils G. Morgenthaler, Joachim Struck, Christine Alonso, and Andreas Bergmann, Assay for the measurement of copeptin, a stable peptide derived from the precursor of vasopressin, Clinical Chemistry 52: 112-119, 2006).

Neurophysin has been described as a marker for nicotine uptake (Robinson A. G., Isolation, assay, and secretion of individual human neurophysins, J Clin Invest 1975; 55: 360-367), malignancy- and nonmalignancy-related syndrome of inappropriate ADH secretion (SIADH), and nephrogenic diabetes insipidus (Pullan P. T., Clappison B. H., Johnston C. I., Plasma vasopressin and human neurophysins in physiological and pathological states associated with changes in vasopressin secretion, J Clin Endocrinol Metab 1979; 49: 580-587; North W. G., LaRochelle F. T., Jr., Melton J., Mills R. C., Isolation and partial characterization of two human neurophysins: their use in the development of specific radioimmunoassays. J Clin Endocrinol Metab 1980; 51: 884-891).

However, a disadvantage of the known diagnostic methods using the markers known heretofore is that early and complete identification of at-risk patients is not achieved, and therefore risk stratification is inadequate. An object of the invention, therefore, is to develop a method for risk stratification for acute coronary syndrome which allows improved identification of at-risk patients.

A further disadvantage is that in the prior art, sufficient sensitivity and/or specificity of the markers is usually not achieved.

A further object, therefore, is to provide a method for risk stratification for acute coronary syndrome, wherein at least one marker or a combination of markers has sufficient sensitivity and specificity in an in vitro diagnosis.

SUMMARY OF THE INVENTION

The object of the present invention, therefore, is to provide a method for risk stratification for acute coronary syndrome. The object is achieved by use of a method for risk stratification for acute coronary syndrome, wherein provasopressin (proAVP) or fragments and partial peptides thereof, in particular copeptin or neurophysin II, is determined by an in vitro diagnosis (referred to below as "method according to the invention").

Surprisingly, provasopressin (proAVP) or fragments and partial peptides thereof, in particular copeptin or neurophysin II, has high sensitivity and specificity for the diagnosis of acute coronary syndrome (see the examples and figures).

The term "acute coronary syndrome" encompasses various phases of coronary heart disease which are immediately life-threatening. This concerns in particular emergency medical care, specifically, acute myocardial infarction and/or angina pectoris, as well as sudden cardiac death. In addition to acute myocardial infarction, which according to WHO criteria (WHO (1979): Nomenclature and criteria for diagnosis of ischemic heart disease, Report of the Joint International Society and Federation of Cardiology/World Health Organization task force on standardization of clinical nomenclature, Circulation 59 (3): 607-609) is defined as an acute chest pain event lasting longer than 20 minutes in conjunction with ST segment elevation and/or an increase in myocardial enzymes, the term "unstable angina pectoris" (AP) has become established, which according to the invention is interpreted as "acute coronary syndrome" (Hamm C. W.: Leitlinien: Akutes coronary syndrome (ACS)—Teil 1: ACS ohne persistierende ST-Hebung [Guidelines: Acute coronary syndrome (ACS)– Part 1: ACS without persistent ST elevation], Z Kardiol (2004) 93: 72-90; see also: Pschyrembel, De Gruyter, Berlin 2004).

According to the invention, the term "risk stratification" encompasses the identification of patients, in particular emergency care and at-risk patients, with an unfavorable prognosis, for intensive diagnostics and for therapy/treatment of acute coronary syndrome, in particular myocardial infarction, and angina pectoris with the objective of enabling an optimal clinical outcome. Risk stratification according to the invention thus allows effective treatment methods for acute coronary syndrome, using percutaneous coronary intervention and the newest medicaments.

The invention therefore further relates to the identification of patients with increased risk and/or unfavorable prognosis of acute coronary syndrome, in particular myocardial infarction and angina pectoris, and symptomatic and/or asymptomatic patients, in particular emergency care patients.

Figure 1:
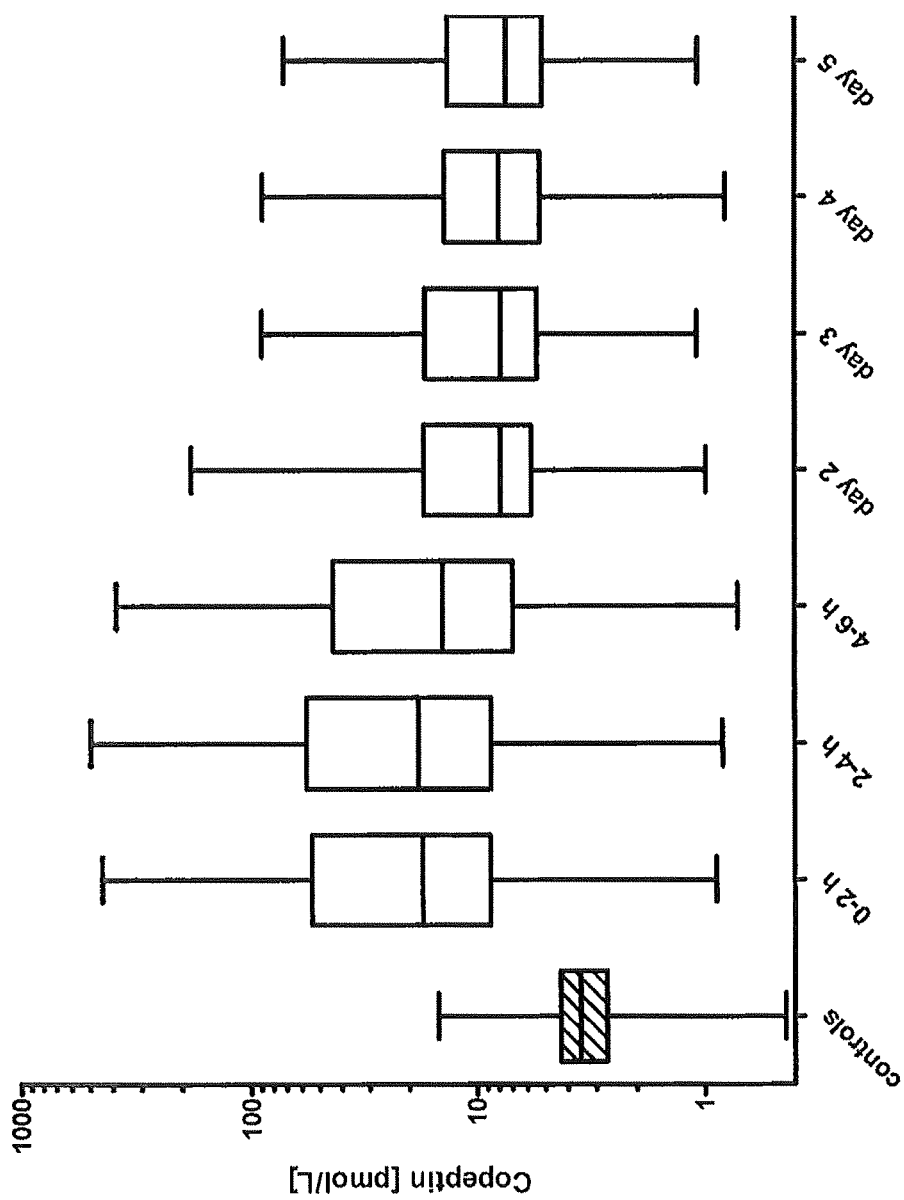
FIG. 1 shows a graph of copeptin values in patients following myocardial infarction. Plasma samples were collected from 131 patients, as stated, at various times following myocardial infarction. Copeptin values in healthy subjects (controls; 200 values) are also plotted. Copeptin values for the groups are illustrated as box-and-whisker plots.

Also illustrated are copeptin values in healthy subjects (controls; 200 values). Copeptin values for the groups are illustrated as box-and-whisker plots.

FIG. 3 shows the amino acid sequence of preprovasopressin (164 amino acids) (SEQ ID NO: 3) and the partial peptides and fragments of proAVP (amino acids: 29 164), neurophysin II (amino acids: 32-124) (SEQ ID NO: 2), and copeptin (amino acids: 126-164) (SEQ ID NO: 1).

DETAILED DESCRIPTION OF THE INVENTION

The method according to the invention may be used in a particularly advantageous manner to provide reliable stratification in emergency and/or intensive medical care. The method according to the invention thus allows clinical decisions resulting in rapid therapeutic success and avoidance of mortalities. Such clinical decisions also include further treatment with medicaments for treatment or therapy of acute coronary syndrome, in particular acute myocardial infarction (AMI) and angina pectoris (AP).

The invention therefore further relates to a method for risk stratification in patients with acute coronary syndrome for making clinical decisions such as further treatment and therapy with medicaments, preferably in time-critical intensive or emergency medical care.

In one further preferred embodiment, the method according to the invention therefore relates to therapeutic control of acute coronary syndrome, in particular acute myocardial infarction (AMI) and angina pectoris (AP).

In one further preferred embodiment of the method according to the invention, risk stratification is carried out for prognosis, differential diagnostic early detection and identification, severity assessment, and prognostic assessment in conjunction with therapy.

In one further preferred embodiment, the invention relates to a method for in vitro diagnostics for early or differential diagnosis or prognosis of myocardial infarction or angina pectoris, wherein the marker provasopressin (proAVP) or fragments and partial peptides thereof, in particular copeptin or neurophysin II, is determined in a patient to be studied. However, copeptin or a fragment or partial sequence thereof, or neurophysin II or a fragment or partial sequence thereof, is particularly preferred.

The invention further relates to a method for risk stratification for acute coronary syndrome or a method for in vitro diagnostics for early or differential diagnosis or prognosis of myocardial infarction or angina pectoris according to one of the above embodiments, wherein after the appearance of symptoms a cutoff (threshold value) range of 6-20 pmol/L of the marker provasopressin (proAVP) or fragments and partial peptides thereof, in particular copeptin or neurophysin II, is significant (specific) for the diagnosis and/or risk stratification. Also preferred is a cut-off (threshold value) of 6-20 pmol/L, in particular 7.5 pmol/L, preferably up to 2 hours after the appearance of symptoms.

The invention further relates to a method for risk stratification for acute coronary syndrome or a method for in vitro diagnostics for early or differential diagnosis or prognosis of myocardial infarction or angina pectoris according to one of the above embodiments, wherein after the appearance of symptoms a cutoff (threshold value) range of 10-30 pmol/L of the marker provasopressin (proAVP) or fragments and partial peptides thereof, in particular copeptin or neurophysin II, is significant (specific) for the prognosis and/or risk stratification. Also preferred is a cut-off (threshold value) of 10-20 pmol/L. On this basis these methods according to the invention are advantageously sensitive.

In one embodiment of the method according to the invention, bodily fluid, in particular blood, optionally whole blood or serum or collectable plasma, is withdrawn from the patient to be studied, and the diagnosis is made in vitro/ex vivo, i.e., outside the human or animal body. As a result of the determination of the marker provasopressin (proAVP) or fragments and partial peptides thereof, in particular copeptin or neurophysin II, high sensitivity and specificity for acute coronary syndrome, myocardial infarction, and angina pectoris are achieved, and diagnosis or risk stratification may be performed based on the quantity present in at least one patient sample. However, the marker copeptin (stable fragment of proAVP or preprovasopressin) or a fragment or partial sequence thereof is very particularly preferred. Also particularly preferred is the marker neurophysin (stable fragment of proAVP or preprovasopressin) or a fragment or partial sequence thereof.

Within the scope of the invention, "provasopressin" is understood to mean a human protein or polypeptide which may be obtained from preprovasopressin, and for preprovasopressin includes amino acids 29-164 (also see WO 2006/018315 and FIG. 3) and fragments or partial peptides obtainable therefrom, in particular copeptin (fragment: amino acids 126-164 (39 amino acids: SEQ: ASDRSNATQL DGPAGALLLR LVQLAGAPEP FEPAQPDAY (SEQ ID NO: 1)) or neurophysin II (fragment: amino acids 32-124 of preprovasopressin (93 amino acids: SEQ: AMSDLELRQC LPCGPGGKGR CFGPSICCAD ELGCFVGTAE ALRCQEENYL PSPCQSGQKA CGSGGRCAAF GVCCNDESCV TEPECREGFH RRA (SEQ ID NO: 2)). These polypeptides according to the invention may also have post-translational modifications such as glycolization, lip(o)idization, or derivatization.

In one further preferred embodiment the invention relates to the diagnosis and/or risk stratification and/or early or differential diagnosis and/or prognosis for acute coronary syndrome, in particular acute myocardial infarction (AMI) and angina pectoris (AP), wherein neurophysin is determined in a patient to be studied.

In one further embodiment, provasopressin (proAVP) or fragments and partial peptides thereof, in particular copeptin or neurophysin II, may also be determined using additional markers, preferably those which already indicate acute coronary syndrome, in particular myocardial infarction or angina pectoris.

The invention therefore relates to such an embodiment of the method according to the invention, wherein the determination is also carried out using at least one additional marker selected from the group of inflammatory markers, cardiovascular markers, neurohormonal markers, or ischemic markers in a patient to be studied.

According to the invention, the inflammatory marker may be selected from the group comprising C-reactive protein (CRP), cytokines such as TNF-alpha, interleukins such as IL-6, procalcitonin (1-116, 3-116), and adhesion molecules such as VCAM or ICAM; and the cardiovascular marker, in particular a marker which indicates necrosis of cardiac muscle tissue, and a marker which influences blood pressure, may be selected from the group comprising creatin kinase, myoglobin, myeloperoxidase, natriuretic protein, in particular ANP (or ANF), proANP, NT-proANP, BNP, proBNP, or NT-proBNP, or in each case a partial sequence thereof, cardiac troponin, or CRP. Also included are circulation-regulating (pro)hormones, in particular progastrin-releasing peptide (proGRP), pro endothelin-1, proleptin, proneuropeptide-Y, prosomatostatin, proneuropeptide-YY, proopiomelanocortin, proadrenomedullin (proADM), or in each case a partial sequence thereof. The ischemic marker may be selected from at least one marker from the group comprising troponin I and T, and CK-MB. In addition, the neurohormonal marker may be at least one natriuretic protein, in particular ANP (or ANF), proANP, NT-proANP, BNP, proBNP, or NT-proBNP, or in each case a partial sequence thereof.

In one particularly preferred embodiment, the invention relates to a particularly advantageous combination of biomarkers and provasopressin (proAVP) or fragments and partial peptides thereof, in particular copeptin or neurophysin II, with natriuretic proteins, ANP (or ANF), proANP, NT-proANP, BNP, proBNP, or NT-proBNP, or in each case a partial sequence thereof.

The invention therefore relates to a method for in vitro diagnosis of acute coronary syndrome, myocardial infarction, or angina pectoris, wherein the marker provasopressin (proAVP) or fragments and partial peptides thereof, in particular copeptin or neurophysin II, in combination with natriuretic proteins, in particular ANP (or ANF), proANP, NT-proANP, BNP, proBNP, or NT-proBNP, or in each case a partial sequence thereof, is determined in a patient to be studied. Once again, a combination of neurophysin II, copeptin, and BNP, proBNP, or NT-proBNP, in particular copeptin and proBNP, is particularly preferred.

It is particularly advantageous that the referenced biomarker combinations have synergies which result in improved specificity and sensitivity for the diagnosis of the [ ][1] (see examples).

[1] Translator's note: Apparent omission in source document.

In a further embodiment of the invention, for an in vitro diagnosis the method according to the invention may be carried out by means of parallel or simultaneous determinations of the markers (for example, using multititer plates containing 96 or more cavities), wherein the determinations are carried out for at least one patient sample.

In addition, the method according to the invention and determinations therefor may be carried out in a diagnostic device based on an automatic analyzer, in particular using a Kryptor system (kryptor.net).

In a further embodiment, the method according to the invention and determinations therefor may be carried out using a rapid test (for example, a lateral flow test) in either single- or multi-parameter determinations. One particularly preferred embodiment involves a self-test, or a device which is suitable for emergency care diagnostics.

The invention further relates to the use of provasopressin (proAVP) or fragments and partial peptides thereof, in particular copeptin or neurophysin II, for risk stratification for acute coronary syndrome, myocardial infarction, or angina pectoris, and/or for in vitro diagnostics for early or differential diagnosis or prognosis of myocardial infarction or angina pectoris.

In one special embodiment the invention relates to the use of provasopressin (proAVP) or fragments and partial peptides thereof, in particular copeptin or neurophysin II, in combination with natriuretic proteins, in particular ANP (or ANF), proANP, NT-proANP, BNP, proBNP, or NT-proBNP, or in each case a partial sequence thereof, for diagnosis and/or risk stratification for acute coronary syndrome, myocardial infarction, or angina pectoris.

A further object is to provide a corresponding diagnostic device for carrying out the methods according to the invention.

Within the scope of the invention, such a diagnostic device, in particular an array or assay (for example, immunoassay, ELISA, etc.), is understood in the broadest sense as a device for carrying out the methods according to the invention.

The invention further relates to a kit for risk stratification for acute coronary syndrome, myocardial infarction, and/or angina pectoris, containing detection reagents for determining provasopressin (proAVP) or fragments and partial peptides thereof, in particular copeptin or neurophysin II, and optionally the additional markers stated above. Such detection reagents include antibodies, for example.

In one special embodiment the invention relates to a kit for diagnosis and/or risk stratification for acute coronary syndrome, myocardial infarction, and/or angina pectoris, containing detection reagents for determining provasopressin (proAVP) or fragments and partial peptides thereof, in particular copeptin or neurophysin II in combination with natriuretic proteins, in particular ANP (or ANF), proANP, NT-proANP, BNP, proBNP, or NT-proBNP, or in each case a partial sequence thereof, and optionally the additional markers stated above. Such detection reagents include antibodies, for example.

The following examples and figures are used for a more detailed explanation of the invention, but do not limit the invention to said examples and figures.

Examples and Figures:

Patients admitted into emergency care of a hospital with the primary symptom of chest pain had a blood sample taken during the initial examination.

131 patients with myocardial infarction (MI) (median age: 64.0 years) were observed for the appearance of acute MI symptoms over a total period of 180 days:

Within the first 6 hours after appearance of symptoms (chest pain) and admittance to the hospital, 3 blood withdrawals were made, one each at 0-2 hours, 2-4 hours, and 4-6 hours after appearance of MI symptoms.

Copeptin and NT-ProBNP were determined in each case.

After hospitalization, within the first 4 days after therapeutic intervention (standard, see Braunwald et al., 2002) (day 2-5), in each case one blood withdrawal with subsequent copeptin determination was performed.

After dismissal (median hospital stay: 7.2 days), the patients were observed over a period of 180 days. The development of severe cardiac sufficiency and/or death of the patient were determined to be events. Of the observed patients, 115 had no events (o.E.) and 16 had events (+E.). The median ages of the groups were 63.8 and 64.5 years.

Figure 2:
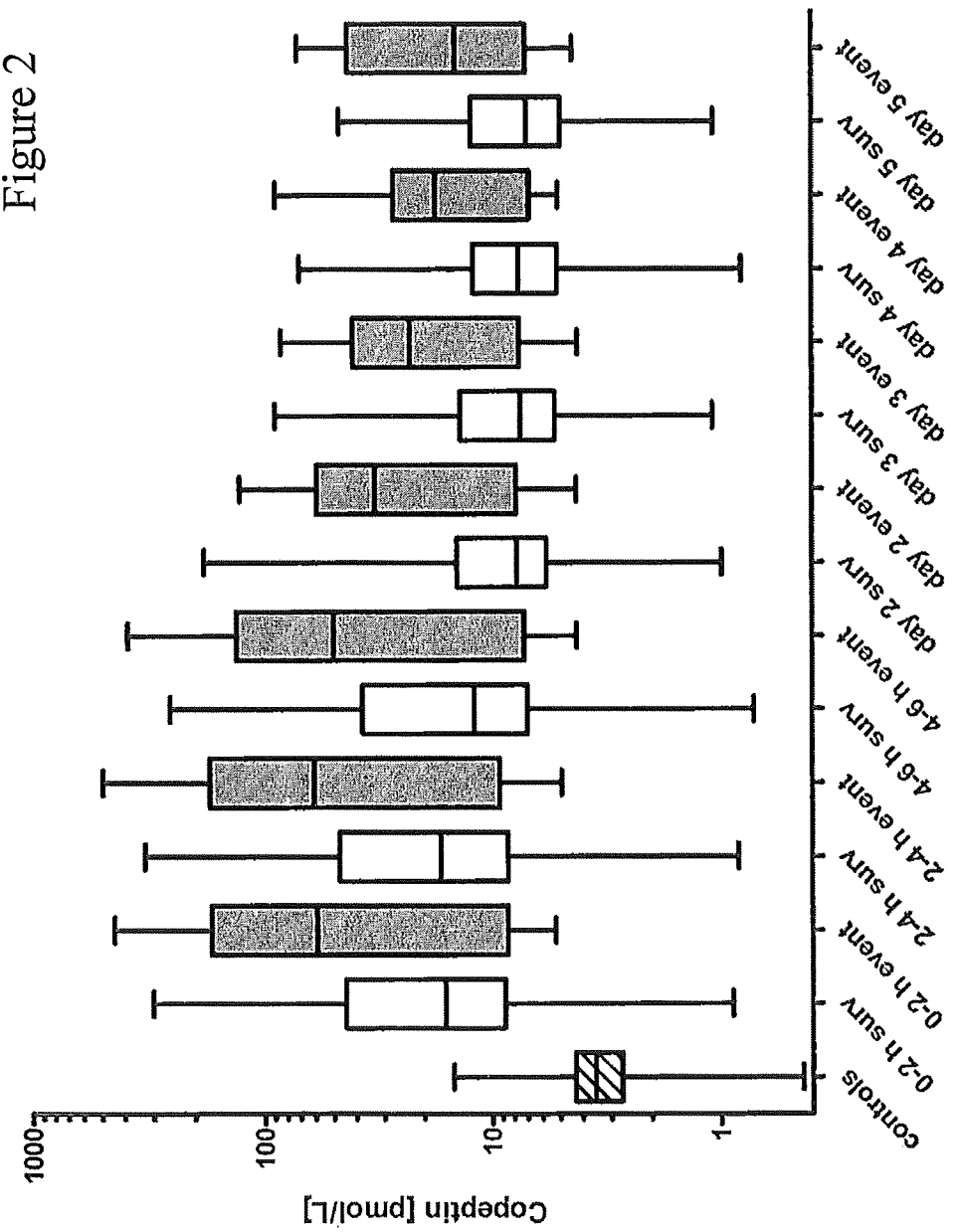
FIG. 2 shows a graph of copeptin values in patients following cardiac infarction. Plasma samples were collected, as stated, at various times following myocardial infarction. The patients were then classified into groups indicating whether death or rehospitalization due to cardiac insufficiency subsequently occurred ("event"; 16 patients) or did not occur ("surv"; 115 patients).

For evaluating the diagnostic effectiveness of the biomarkers for the early diagnosis of MI and for risk stratification, the results from individual patient blood withdrawals were compared to those from 200 individuals (median age: 65.2 years) who showed no symptoms of MI (controls). The results are shown in Table 1 and FIGS. 1 and 2.

Table 1 shows the sensitivities (values>cutoff (threshold value)) for MI patients compared to the corresponding specificities (values<cutoff (threshold value)) for the controls at the indicated times after appearance of symptoms.

Within the earliest observation period (0-2 hours) the copeptin was greatly elevated compared to the controls. For example, only 4.5% of all controls exhibited a copeptin value greater than 7.5 pmol/L (example cutoff (threshold value)) (specificity=95.5%), whereas 78.3% of the patients without subsequent events, and even 87.5% of the patients with events, exhibited copeptin concentrations greater than 7.5 pmol/L (sensitivity). Compared to the markers used thus far in routine diagnostics (troponin, myoglobin, CK-MB), this resulted in surprising increases in the sensitivities at points in time which then allowed these biomarkers to be used for early or differential diagnosis of MI, as well as for risk stratification for acute coronary syndrome (troponin; CK-MB generally appeared only after 6 hours post-event, while myoglobin appeared early with less sensitivity, but then dropped again approximately 2 hours later; i.e., resulted in an uncertain diagnostic window). Advantageously, the increase in copeptin, i.e., the time of the blood withdrawal, was of secondary importance for early diagnostics (at the 7.5 pmol/L cutoff, for example, 78.3/80.0/73% sensitivity at 0-2/2-4/4-6 hours, respectively).

Combination with proBNP or NT-ProBNP

Surprisingly, it was shown that the combination of copeptin with proBNP (NT-ProBNP) allowed a marked increase in the sensitivity of early diagnosis of MI (see Table 1). Although proBNP (NT-ProBNP) was inferior to the diagnostic effectiveness of copeptin, for the evaluation of copeptin>7.5 pmol/L and/or proBNP (NT-ProBNP)>200 pmol/mL, for example, at a specificity of approximately 95% which was comparable to the corresponding individual markers, it allowed an increase of 3-6% in the sensitivities at all times in the non-event group, and in the event group, an increase of 6-9.5% compared to the sensitivities of copeptin as an individual marker.

Sample Recovery, Biomarker Analysis:

Blood withdrawals were made using standard serum monovettes. After a clotting time of 20-40 min, centrifugation was performed for 15 min at 2000 g, followed by serum separation by decanting. The serum samples were stored at −20° C. for further use.

NT-ProBNP was determined according to Omland et al. (Omland T., Persson A., Ng L., et al., N-terminal pro-B-type natriuretic peptide and long-term mortality in acute coronary syndromes, Circulation, 2002; 106: 2913-2918) using a luminescence immunoassay.

Copeptin was determined using the copeptin luminescence immunoassay from BRAHMS AG. The copeptin determination method is described in detail in Morgenthaler N. G. et al., Clin. Chem. 2006 January, 52 (1), 112-119. In summary: a 50-microliter sample was pipetted into a test tube coated with copeptin antibody (AB1) and mixed with 200 microliters of a solution of acridinium ester-marked anti-copeptin antibody (AB2) and incubated for 2 hours at room temperature. After removal of unbound (free) marked antibody by washing four times with wash solution (Lumitest wash solution, Brahms AG), bound acridinium ester-marked antibody was determined in a luminometer from Berthold.

Prognosis (Prediction of Event Occurrence):

Surprisingly, it was shown that MI patients with events within the 180 days post hospitalization exhibited even higher copeptin concentrations than patients without events. Within 6 hours after appearance of MI symptoms, at the example cutoff (threshold value) of 30 pmol/L copeptin showed a relative risk of approximately 1:2 (patients with copeptin>30 had twice the risk for subsequent events compared to patients<30 pmol/L).

As expected, the concentrations decreased after the intervention (day 2ff., Table 2b). In this case it was surprisingly shown that patients with subsequent events exhibited a much lower reduction in the biomarker. This led to a sharp increase in risk, to values of up to 1:7.14 for patients with a copeptin value higher than 30 pmol/L.

TABLE 1

|  | 0-2 h o.E. | 0-2 h +E. | 2-4 h o.E. | 2-4 h +E. | 4-6 h o.E. | 4-6 h +E. | Controls (specificity) |
| --- | --- | --- | --- | --- | --- | --- | --- |
| Copeptin (pmol/L) | | | | | | | |
| Sens/Spef for cutoff 6 | 88.7% | 93.8% | 89.6% | 93.8% | 80.0% | 87.5% | 93.0% |
| Sens/Spef for cutoff 7.5 | 78.3% | 87.5% | 80.0% | 87.5% | 73.0% | 75.0% | 95.5% |
| Sens/Spef for cutoff 10 | 67.0% | 68.8% | 68.7% | 68.8% | 56.5% | 68.8% | 97.5% |
| Sens/Spef for cutoff 20 | 44.3% | 8.8% | 43.5% | 68.8% | 40.0% | 62.5% | 100.0% |
| NT-ProBNP (pmol/mL), cutoff 200 | 58.5% | 62.0% | 61.5% | 65.0% | 66.5% | 70.0% | 94.5% |
| Combination: copeptin >7.5 pmol/L and/ or NT-ProBNP >200 pmol/mL | 81.2% | 93.5% | 83.5% | 96.0% | 79.5% | 84.5% | 93.8% |

TABLE 2a

| Copeptin | 0-2 h +E. | 0-2 h o.E. | 2-4 h +E. | 2-4 h o.E. | 4-6 h +E. | 4-6 h o.E. |
|---|---|---|---|---|---|---|
| Patients >30 pmol/L | 62.5% | 36.5% | 62.5% | 35.7% | 62.5% | 27.8% |
| Relative risk for cardiac insufficiency or death up to 180 days after dismissal from the hospital | 1.7 | | 1.75 | | 2.25 | |

TABLE 2b

| Copeptin | Day 2 +E. | Day 2 o.E. | Day 3 +E. | Day 3 o.E. | Day 4 +E. | Day 4 o.E. | Day 5 +E. | Day 5 o.E. |
|---|---|---|---|---|---|---|---|---|
| Patients >30 pmol/L | 50.0% | 7.0% | 43.8% | 7.0% | 39.2% | 6.1% | 31.3% | 6.1% |
| Relative risk for cardiac insufficiency or death up to 180 days after dismissal from the hospital | 7.14 | | 6.26 | | 6.42 | | 5.13 | |

Legend in tables and figures: surv.=survival, E.=event: death, development of severe cardiac insufficiency, cutoff=threshold value in pmol/L, Sens=sensitivity, Spef=specificity, o.=without.

Neurophysin:

A radioimmunoassay for neurophysin was prepared according to earlier descriptions (Pullan (supra)): neurohypophysis neurophysin was isolated and quantified. In this manner rabbits were immunized, resulting in recovery of high-titer anti-neurophysin antisera. The highest-titer antiserum was used in a concentration of 1:100,000 for the immunoassay. Purified neurophysin was radioiodized using the chloramine T method and used as a tracer in the assay. Dilutions of purified neurophysin in standard equine serum were used as standards. The assay was carried out as follows: A 50-1.1 μL sample or standard was mixed with 100 μL tracer (12,000 dpm per determination) and 100 μL, diluted anti-neurophysin antiserum, and incubated for 24 hours at 4° C. 100 mM sodium phosphate, pH 7.5, and 0.1% BSA were used as buffer. An antibody-bound tracer was separated from free tracer by adding 60% ethanol and then centrifuging for 15 minutes at 4° C. and 5,000 g. The supernatant was discarded, and the residual radioactivity in the pellet was determined. The analysis was performed using Multicalc software. The assay had an analytical detection limit of 22 pg/mL. The assay had a measurement range up to 400 pg/mL. The assay was used to measure plasma samples from various patients as described below. Samples with measured values>400 pg/mL were measured in suitable dilutions, resulting in measured values within the measurement range.

Myocardial Infarction/Diagnosis

In 66 patients with acute cardiac infarction, samples were taken no later than 6 hours after occurrence of the cardiac infarction, and neurophysin was measured. For purposes of comparison, neurophysin was determined in 200 healthy controls. The receiver operating characteristics analysis for diagnosis of cardiac infarction resulted in an AUC of 0.95. For a cutoff value of 213 pg/mL, a sensitivity of 62.6% was obtained at a specificity of 98%. For a cutoff value of 136.1 pg/mL a sensitivity of 84% was obtained at a specificity of 95%.

Myocardial Infarction/Prognosis

In 66 patients with acute cardiac infarction, samples were taken no later than 6 hours after onset of the cardiac infarction or on the second day after the infarction, and neurophysin was measured. The patients were observed for a period of 360 days. During this period 58 patients had no adverse event, and 8 died or were rehospitalized due to cardiac insufficiency.

Prognosis for Day 1 (<6 Hours after Occurrence of the Infarction):

Receiver operating characteristics analysis was used to determine the best cutoff value (defined as the largest product of the sensitivity and specificity) for prognosis of mortality or rehospitalization due to cardiac insufficiency: 777 pg/mL. At this cutoff value the sensitivity of the prognosis was 62.5%, and the specificity was 73%. The likelihood ratio of an adverse event at a cutoff value of 777 pg/mL was 2.3.

Prognosis for Day 2:

Receiver operating characteristics analysis was used to determine the best cutoff value (defined as the largest product of the sensitivity and specificity) for prognosis of mortality or rehospitalization due to cardiac insufficiency: 261 pg/mL. At this cutoff value the sensitivity of the prognosis was 68.8%, and the specificity was 73%. The likelihood ratio of an adverse event at a cutoff value of 261 pg/mL was 2.6.

The invention claimed is:

1. A method for in vitro diagnosis of acute coronary syndrome, myocardial infarction, or angina pectoris, comprising
   a) determining the level of neurophysin II in at least one sample from a patient, wherein said neurophysin II is a fragment of preprovasopressin, said fragment consisting of the polypeptide of SEQ ID NO: 2; and b) diagnosing the presence of acute coronary syndrome, myocardial infarction or angina pectoris in said patient based on the result in step a).

2. The method of claim 1, further comprising determining the level of a natriuretic protein or a partial sequence thereof in at least one sample from said patient.

3. The method of claim 1, wherein a threshold level of neurophysin II of 6-20 pmol/L in said at least one sample indicates the presence of acute coronary syndrome, myocardial infarction, or angina pectoris in said patient.

4. The method of claim 3, wherein said threshold level is 6-10 pmol/L of neurophysin II.

5. The method of claim 1, further comprising determining the level of at least one additional marker selected from the group consisting of inflammatory markers, cardiovascular markers, neurohormonal markers, and ischemic markers in at least one sample from said patient.

6. The method of claim 5, wherein said inflammatory marker is selected from the group consisting of C-reactive protein (CRP), cytokines, interleukins, procalcitonin (1-116, 3-116), and adhesion molecules.

7. The method of claim 5, wherein the cardiovascular marker is at least one marker selected from the group consisting of creatin kinase, myoglobin, myeloperoxidase, a natriuretic protein, cardiac troponin, CRP, circulation-regulating (pro)hormones and, in each case, a partial sequence thereof.

8. The method of claim 5, wherein the ischemic marker is at least one marker selected from the group consisting of troponin I and T, and CK-MB.

9. The method of claim 6, wherein the neurohormonal marker is at least one natriuretic protein or a partial sequence thereof.

* * * * *

SEQUENCE LISTING

<160> NUMBER OF SEQ ID NOS: 3

<210> SEQ ID NO 1
<211> LENGTH: 39
<212> TYPE: PRT
<213> ORGANISM: Homo sapiens

<400> SEQUENCE: 1

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
            20                  25                  30

Pro Ala Gln Pro Asp Ala Tyr
            35

<210> SEQ ID NO 2
<211> LENGTH: 93
<212> TYPE: PRT
<213> ORGANISM: Homo sapiens

<400> SEQUENCE: 2

Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
            20                  25                  30

Gly Cys Phe Val Gly Thr Ala Glu Ala Leu Arg Cys Gln Glu Glu Asn
            35                  40                  45

Tyr Leu Pro Ser Pro Cys Gln Ser Gly Gln Lys Ala Cys Gly Ser Gly
50                  55                  60

Gly Arg Cys Ala Ala Phe Gly Val Cys Cys Asn Asp Glu Ser Cys Val
65                  70                  75                  80

Thr Glu Pro Glu Cys Arg Glu Gly Phe His Arg Arg Ala
            85                  90

<210> SEQ ID NO 3
<211> LENGTH: 164
<212> TYPE: PRT
<213> ORGANISM: Homo sapiens

<400> SEQUENCE: 3

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Pro Ala
            20                  25                  30

Met Ser Asp Leu Glu Leu Arg Gln Cys Leu Pro Cys Gly Pro Gly Gly
            35                  40                  45

Lys Gly Arg Cys Phe Gly Pro Ser Ile Cys Cys Ala Asp Glu Leu Gly
50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
            85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
            115                 120                 125

Arg Ser Asn Ala Thr Gln Leu Asp Gly Pro Ala Gly Ala Leu Leu Leu
            130                 135                 140

Arg Leu Val Gln Leu Ala Gly Ala Pro Glu Pro Phe Glu Pro Ala Gln
145                 150                 155                 160

Pro Asp Ala Tyr